(12) United States Patent
Merkel et al.

(10) Patent No.: US 8,114,308 B2
(45) Date of Patent: Feb. 14, 2012

(54) AZEOTROPE-LIKE COMPOSITION OF 2,3-DICHLORO-3,3-DIFLUOROPROPENE (HCFO-1232XF) AND HYDROGEN FLUORIDE (HF)

(75) Inventors: Daniel C. Merkel, Orchard Park, NY (US); Hang T. Pham, Amherst, NY (US); Ryan Hulse, Getzville, NY (US); Rajiv R. Singh, Getzville, NY (US); Konstantin A. Pokrovski, Orchard Park, NY (US); Hsueh S. Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 136 days.

(21) Appl. No.: 12/749,640

(22) Filed: Mar. 30, 2010

(65) Prior Publication Data
US 2011/0240902 A1  Oct. 6, 2011

(51) Int. Cl.
*C09K 5/04* (2006.01)
*B01F 1/00* (2006.01)
*B01D 53/70* (2006.01)

(52) U.S. Cl. .......... 252/67; 252/364; 510/177; 510/408; 423/240 R

(58) Field of Classification Search ............. 252/67, 252/364; 510/177, 408; 423/240 R
See application file for complete search history.

(56) References Cited

U.S. PATENT DOCUMENTS

| 7,476,771 | B2 | 1/2009 | Miller et al. | |
| 2007/0007488 | A1 | 1/2007 | Singh et al. | |
| 2007/0197842 | A1 | 8/2007 | Mukhopadhyay et al. | |
| 2009/0030247 | A1* | 1/2009 | Johnson et al. | 570/155 |
| 2009/0182179 | A1* | 7/2009 | Merkel et al. | 570/168 |
| 2009/0211988 | A1 | 8/2009 | Pham et al. | |
| 2009/0224207 | A1* | 9/2009 | Pham et al. | 252/372 |
| 2009/0227822 | A1 | 9/2009 | Pham et al. | |
| 2009/0240090 | A1 | 9/2009 | Merkel et al. | |
| 2009/0242832 | A1* | 10/2009 | Pham et al. | 252/182.12 |
| 2009/0256110 | A1* | 10/2009 | Merkel et al. | 252/182.12 |
| 2009/0312585 | A1* | 12/2009 | Merkel et al. | 570/167 |
| 2010/0036179 | A1* | 2/2010 | Merkel et al. | 570/156 |
| 2010/0137658 | A1* | 6/2010 | Merkel et al. | 570/175 |
| 2010/0331583 | A1* | 12/2010 | Johnson et al. | 570/156 |
| 2011/0207975 | A9* | 8/2011 | Merkel et al. | 570/160 |
| 2011/0210289 | A9* | 9/2011 | Merkel et al. | 252/182.12 |

FOREIGN PATENT DOCUMENTS

| EP | 2108638 A1 | 10/2009 |
| WO | WO 2010123148 A1 * | 10/2010 |
| WO | WO 2010131766 A2 * | 11/2010 |
| WO | WO 2011087825 A1 * | 7/2011 |

OTHER PUBLICATIONS

CAS reg. No. 2252-87-1, Nov. 16, 1984.*

* cited by examiner

*Primary Examiner* — Douglas Mc Ginty
(74) *Attorney, Agent, or Firm* — Bruce Bradford

(57) ABSTRACT

Provided are azeotropic and azeotrope-like compositions of 2,3-dichloro-3,3-difluoropropene (HCFO-1232xf) and hydrogen fluoride (HF). Such azeotropic and azeotrope-like compositions are useful as intermediates in the production of 2,3,3,3-tetrafluoropropene (HFO-1234yf).

35 Claims, 1 Drawing Sheet

AZEOTROPE-LIKE COMPOSITION OF 2,3-DICHLORO-3,3-DIFLUOROPROPENE (HCFO-1232XF) AND HYDROGEN FLUORIDE (HF)

FIELD OF THE INVENTION

The present invention pertains to azeotropic and azeotrope-like compositions of 2,3-dichloro-3,3-difluoropropene (HCFO-1232xf) and hydrogen fluoride (HF). More particularly the invention pertains to such azeotropic and azeotrope-like compositions which are useful as intermediates in the production of 2,3,3,3-tetrafluoropropene (HFO-1234yf).

BACKGROUND OF THE INVENTION

Traditionally, chlorofluorocarbons (CFCs) like trichlorofluoromethane and dichlorodifluoromethane have been used as refrigerants, blowing agents and diluents for gaseous sterilization. In recent years there has been universal concern that completely halogenated chlorofluorocarbons might be detrimental to the Earth's ozone layer. Therefore, stratospherically safer alternatives to these materials are desirable. Consequently, there is a worldwide effort to use fluorine-substituted hydrocarbons which contain fewer or no chlorine substituents. In this regard, 2,3-dichloro-3,3-difluoropropene (HCFO-1232xf), having low ozone depletion potential, is being considered as a replacement for chlorofluorocarbons such as dichlorodifluoromethane in refrigeration systems and trichlorofluoromethane as a blowing agent. The production of HFC's, i.e. compounds containing only carbon, hydrogen and fluorine has been the subject of interest to provide environmentally desirable products for use as solvents, blowing agents, refrigerants, cleaning agents, aerosol propellants, heat transfer media, dielectrics, fire extinguishing compositions and power cycle working fluids. It is known in the art to produce fluorocarbons such as HFC's by reacting hydrogen fluoride with various hydrochlorocarbon compounds. Such HFC's are not only considered to be much more environmentally advantageous than hydrochlorofluorocarbons (HCFC's) or chlorofluorocarbons (CFC's) because they are not non-ozone depleting, but also they are non-flammable, and non-toxic as compared to the chlorine containing compounds.

HCFO-1232xf is an intermediate in the production of 2,3,3,3-tetrafluoropropene (HFO-1234yf) which is well known in the art as described in U.S. Published Application No. 20090240090, the contents of which are incorporated herein by reference. HFO-1234yf was previously disclosed to be an effective refrigerant, heat transfer medium, propellant, foaming agent, blowing agent, gaseous dielectric, sterilant carrier, polymerization medium, particulate removal fluid, carrier fluid, buffing abrasive agent, displacement drying agent and power cycle working fluid in U.S. Published Application Nos. 20070007488 and 20070197842, the contents of which are incorporated herein by reference.

It has now been found that an important intermediate in the production of substantially pure HFO-1234yf, is an azeotropic or azeotrope-like composition of 2,3-dichloro-3,3-difluoropropene (HCFO-1232xf) and hydrogen fluoride. This intermediate, once formed, may thereafter be separated into its component parts by known extraction techniques. The azeotropic and azeotrope-like compositions find use not only as intermediates in the production of HFO-1234yf, but they are additionally useful as nonaqueous etchant mixtures for etching semiconductors in the electronics industry, as well as compositions for removing surface oxidation from metals. In addition, the formation of an azeotropic or azeotrope-like composition of HCFO-1232xf and hydrogen fluoride is useful in separating a mixture of HCFO-1232xf from impurities such as one or more halocarbons (e.g. 1,1,1,2,3-pentachloropropane; 1,1,2,3-tetrachloropropene; 2,3,3,3-tetrafluoropropene; 2-chloro-3,3,3-trifluoropropene; 2-chloro-1,1,1,2-tetrafluoropropane; 1,1,1,2,2-pentafluoropropane; or 1,2-dichloro-3,3,3-trifluoropropene). When it is desired to separate a mixture of HCFO-1232xf and an impurity, HF is added to form an azeotropic mixture of HCFO-1232xf and hydrogen fluoride, and then the impurity is removed from the azeotropic mixture, such as by distillation or other known means. This binary azeotrope or azeotrope-like composition is then available for separation into its component parts.

SUMMARY OF THE INVENTION

The invention provides an azeotropic or azeotrope-like composition of hydrogen fluoride and 2,3-dichloro-3,3-difluoropropene.

The invention further provides a method of forming an azeotropic or azeotrope-like composition by forming a blend of about 1 to about 80 weight percent hydrogen fluoride and about 20 to about 99 weight percent 2,3-dichloro-3,3-difluoropropene to thereby form an azeotropic or azeotrope-like composition having a boiling point of from about 0° C. to about 60° C. at a pressure of from about 9 psia to about 65 psia.

The invention also provides a method for removing 2,3-dichloro-3,3-difluoropropene from a mixture containing 2,3-dichloro-3,3-difluoropropene and at least one impurity, by adding hydrogen fluoride to the mixture in an amount sufficient to form an azeotropic or azeotrope-like composition of the 2,3-dichloro-3,3-difluoropropene and the hydrogen fluoride, and thereafter separating the azeotropic composition from the impurity. Impurities may include, but are not limited to, 1,1,1,2,3-pentachloropropane; 1,1,2,3-tetrachloropropene; 2,3,3,3-tetrafluoropropene; 2-chloro-3,3,3-trifluoropropene; 2-chloro-1,1,1,2-tetrafluoropropane; 1,1,1,2,2-pentafluoropropane; or 1,2-dichloro-3,3,3-trifluoropropene.

DETAILED DESCRIPTION OF THE INVENTION

Figure 1:
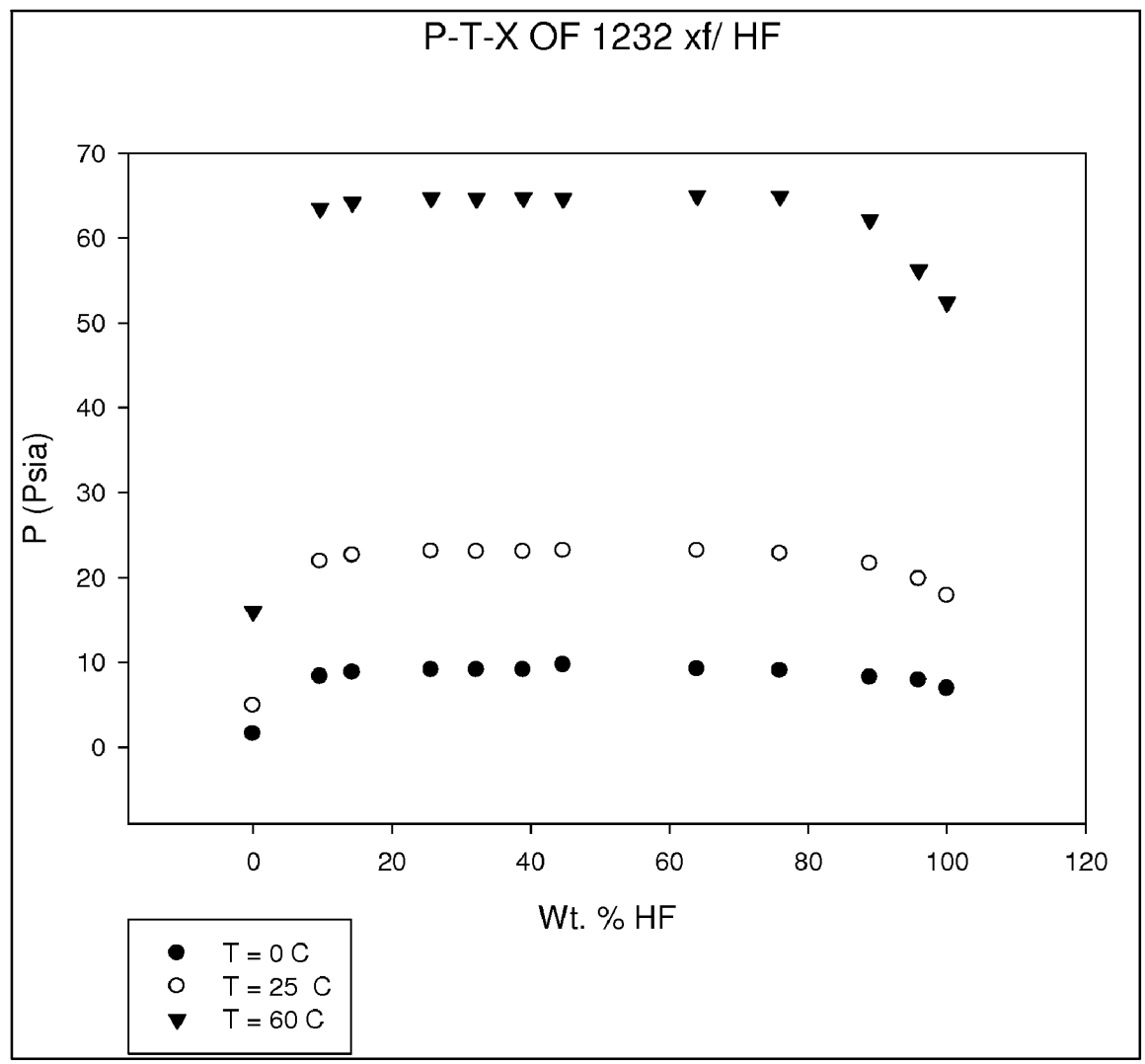
FIG. 1 shows a plot of the vapor pressures of the mixtures formed in Example 2 as measured at 0° C., 25° C. and 60° C.

In a method of preparing an HCFO-1232xf precursor, reagents are fluorinated with hydrogen fluoride. This may be done, for example, by the gas phase catalytic fluorination of $CCl_2=CClCH_2Cl$ with HF to yield HCFO-1232xf. The reaction products of such precursors include HCFO-1232xf, unreacted HF and other by-products. Upon removal of the by-products, a binary azeotrope or azeotrope-like composition of HCFO-1232xf and HF is formed. This binary azeotrope or azeotrope-like composition is then available for separation into its component parts. The azeotropic or azeotrope-like compositions of the HCFO-1232xf and HF are also useful as recycle to the fluorination reactor. Thus, for example, in a process for producing HCFO-1232xf, one can recover a portion of the HCFO-1232xf as an azeotropic or azeotrope-like composition of HCFO-1232xf and HF and then recycle the composition to the reactor.

HCFO-1232xf forms azeotropic and azeotrope-like mixtures with HF. The thermodynamic state of a fluid is defined by its pressure, temperature, liquid composition and vapor composition. For a true azeotropic composition, the liquid composition and vapor phase are essentially equal at a given temperature and pressure range. In practical terms this means that the components cannot be separated during a phase change. For the purpose of this invention, an azeotrope is a liquid mixture that exhibits a maximum or minimum boiling point relative to the boiling points of surrounding mixture compositions. An azeotrope or an azeotrope-like composition is an admixture of two or more different components which, when in liquid form under given pressure, will boil at a substantially constant temperature, which temperature may be higher or lower than the boiling temperatures of the components and which will provide a vapor composition essentially identical to the liquid composition undergoing boiling. For the purpose of this invention, azeotropic compositions are defined to include azeotrope-like compositions which means a composition that behaves like an azeotrope, i.e., has constant-boiling characteristics or a tendency not to fractionate upon boiling or evaporation. Thus, the composition of the vapor formed during boiling or evaporation is the same as or substantially the same as the original liquid composition. Hence, during boiling or evaporation, the liquid composition, if it changes at all, changes only to a minimal or negligible extent. This is in contrast with non-azeotrope-like compositions in which during boiling or evaporation, the liquid composition changes to a substantial degree. Accordingly, the essential features of an azeotrope or an azeotrope-like composition are that at a given pressure, the boiling point of the liquid composition is fixed and that the composition of the vapor above the boiling composition is essentially that of the boiling liquid composition, i.e., essentially no fractionation of the components of the liquid composition takes place. Both the boiling point and the weight percentages of each component of the azeotropic composition may change when the azeotrope or azeotrope-like liquid composition is subjected to boiling at different pressures. Thus, an azeotrope or an azeotrope-like composition may be defined in terms of the relationship that exists between its components or in terms of the compositional ranges of the components or in terms of exact weight percentages of each component of the composition characterized by a fixed boiling point at a specified pressure.

The present invention provides a composition of effective amounts of hydrogen fluoride and HCFO-1232xf to form an azeotropic or azeotrope-like composition. As used herein, effective amount means an amount of each component which, when combined with the other component, results in the formation of an azeotrope or azeotrope-like mixture. In certain embodiments, the inventive compositions are binary azeotropes of only hydrogen fluoride with HCFO-1232xf.

In a certain embodiments, the inventive composition contains from about 1 to about 80 weight percent HF, from about 35 weight percent to about 70 weight percent, or from about 58 weight percent to about 64 weight percent based on the weight of the azeotropic or azeotrope-like composition.

In even further embodiments, the inventive composition contains from about 20 to about 99 weight percent HCFO-1232xf, from about 30 weight percent to about 65 weight percent, or from about 36 weight percent to about 42 weight percent based on the weight of the azeotropic or azeotrope-like composition.

The composition of the present invention has a boiling point of about from 0° C. to about 60° C. at a pressure of about 9 psia to about 65 psia. In one embodiment it has a boiling point of about 0° C. at a pressure of about 9 psia. In another embodiment it has a boiling point of about 25° C. at a pressure of about 23 psia. In a further embodiment it has a boiling point of about 60° C. at a pressure of about 65 psia. An azeotropic or azeotrope-like composition having about 61±3 weight percent HF and about 39±3 weight percent HCFO-1232xf was found at 24° C.

In another embodiment of the invention, 2,3-dichloro-3,3-difluoropropene (HCFO-1232xf) may be removed from a mixture containing 2,3-dichloro-3,3-difluoropropene (HCFO-1232xf) and an impurity which may, for example, result from manufacturing steps in the preparation of 2,3-dichloro-3,3-difluoropropene (HCFO-1232xf). This is done by adding hydrogen fluoride to the mixture of the 2,3-dichloro-3,3-difluoropropene (HCFO-1232xf) and impurity. Hydrogen fluoride is added to the mixture in an amount sufficient to form an azeotropic composition of the 2,3-dichloro-3,3-difluoropropene (HCFO-1232xf) and the hydrogen fluoride, and thereafter the azeotropic composition is separated from the impurity, for example by distillation or other art recognized separating means. In one embodiment, the impurity itself does not form an azeotropic mixture with 2,3-dichloro-3,3-difluoropropene (HCFO-1232xf), hydrogen fluoride or a mixture of 2,3-dichloro-3,3-difluoropropene (HCFO-1232xf) and hydrogen fluoride. In another embodiment, the impurity does form an azeotropic mixture with 2,3-dichloro-3,3-difluoropropene (HCFO-1232xf), hydrogen fluoride or a mixture of 2,3-dichloro-3,3-difluoropropene (HCFO-1232xf) and hydrogen fluoride. Typical impurities of 2,3-dichloro-3,3-difluoropropene (HCFO-1232xf) include, but are not limited to, other halocarbons which may be miscible with 2,3-dichloro-3,3-difluoropropene (HCFO-1232xf) such as, but not limited to, 1,1,1,2,3-pentachloropropane; 1,1,2,3-tetrachloropropene; 2,3,3,3-tetrafluoropropene; 2-chloro-3,3,3-trifluoropropene (HCFO-1233xf); 2-chloro-1,1,1,2-tetrafluoropropane; 1,1,1,2,2-pentafluoropropane; or 1,2-dichloro-3,3,3-trifluoropropene.

The following non-limiting examples serve to illustrate the invention.

EXAMPLE 1

40 g of 2,3-dichloro-3,3-difluoropropene (HCFO-1232x0 were mixed with 60 g of HF to form a heterogeneous azeotrope mixture. The vapor pressure of the mixture at about 25° C. was about 23 psia.

EXAMPLE 2

Binary compositions containing solely 2,3-dichloro-3,3-difluoropropene (HCFO-1232xf) and HF were blended to form a heterogeneous azeotrope mixtures at different compositions. The vapor pressures of the mixtures were measured at about 0, 25 and 60° C. and the following results were noticed. Table 1 shows the vapor pressure measurements of HCFO-1232xf and HF as a function of composition with varying percent HF at constant temperatures of about 0, 25, and 60° C. The data also showed that HCFO-1232xf/HF is a heterogeneous mixture.

TABLE 1

P-T-X of HCFO-1232xf/HF

| | Pressure ( Psia) | | |
|---|---|---|---|
| Weight % HF | T = 0° C. | T = 25° C. | T = 60° C. |
| 0.00 | 1.57 | 4.88 | 15.99 |
| 9.67 | 8.29 | 21.86 | 63.49 |
| 14.33 | 8.78 | 22.59 | 64.16 |
| 25.69 | 9.09 | 23.04 | 64.71 |

TABLE 1-continued

P-T-X of HCFO-1232xf/HF

| Weight % HF | Pressure (Psia) | | |
|---|---|---|---|
| | T = 0° C. | T = 25° C. | T = 60° C. |
| 32.22 | 9.09 | 23.0 | 64.65 |
| 38.96 | 9.1 | 23.0 | 64.74 |
| 44.69 | 9.1 | 23.13 | 64.63 |
| 64.01 | 9.21 | 23.14 | 64.97 |
| 75.93 | 9.0 | 22.76 | 64.92 |
| 88.88 | 8.21 | 21.59 | 62.15 |
| 95.95 | 7.88 | 19.82 | 56.23 |
| 100.0 | 6.87 | 17.82 | 52.43 |

The data also shows that the mixture is azeotropic or azeotrope-like since the vapor pressure of the mixtures of HCFO-1232xf and HF is higher, at all indicated blend proportions, than vapor pressures of HCFO-1232xf and HF alone, i.e. as indicated in the first and last rows of Table 1 when HF is 0.0 wt. % and HCFO-1232xf is at 100.0 wt. % as well as when HCFO-1232xf is at 0.0 wt. % and HF is at 100.0 wt. %. The data from Table 1 is shown in graphic form in FIG. 1.

EXAMPLE 3

The azeotropic or azeotrope-like composition of the HCFO-1232xf/HF mixture was also verified by Vapor-Liquid Equilibrium (VLE) experiment.
47.64 g of 2,3-dichloro-3,3-difluoropropene (HCFO-1232xf) were mixed with 52.36 g of HF to form a heterogeneous mixture (visual observation) at 24° C. The vapor composition was sampled. The result shows that the azeotropic composition is about 60.6±2.0 wt. percent HF at 24° C.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above, and all equivalents thereto.

What is claimed is:

1. An azeotropic or azeotrope-like composition consisting essentially of hydrogen fluoride and 2,3-dichloro-3,3-difluoropropene.

2. An azeotropic or azeotrope-like composition which consists essentially of from about 1 to about 80 weight percent hydrogen fluoride and from about 20 to about 99 weight percent 2,3-dichloro-3,3-difluoropropene, which composition has a boiling point of from about 0° C. to about 60° C. at a pressure of from about 9 psia to about 65 psia.

3. The composition of claim 2 which consists of hydrogen fluoride and 2,3-dichloro-3,3-difluoropropene.

4. The composition of claim 2 wherein the hydrogen fluoride is present in the amount from about 35 to about 70 weight percent.

5. The composition of claim 2 wherein the hydrogen fluoride is present in the amount from about 58 to about 64 weight percent.

6. The composition of claim 2 wherein the 2,3-dichloro-3,3-difluoropropene is present in the amount from about 30 to about 65 weight percent.

7. The composition of claim 2 wherein the 2,3-dichloro-3,3-difluoropropene is present in the amount from about 36 to about 42 weight percent.

8. The composition of claim 2 having a boiling point of about 0° C. at a pressure of about 9 psia.

9. The composition of claim 2 having a boiling point of about 25° C. at a pressure of about 23 psia.

10. The composition of claim 2 having a boiling point of about 60° C. at a pressure of about 65 psia.

11. The composition of claim 2 having about 61±3 weight percent hydrogen fluoride and about 39±3 weight percent 2,3-dichloro-3,3-difluoropropene at 24° C.

12. A method of forming an azeotropic or azeotrope-like composition which comprises forming a blend consisting essentially of from about 1 to about 80 weight percent hydrogen fluoride and from about 20 to about 99 weight percent 2,3-dichloro-3,3-difluoropropene to thereby form an azeotropic or azeotrope-like composition having a boiling point of from about 0° C. to about 60° C. at a pressure of from about 9 psia to about 65 psia.

13. The method of claim 12 wherein the composition consists of hydrogen fluoride and 2,3-dichloro-3,3-difluoropropene.

14. The method of claim 12 wherein the hydrogen fluoride is present in an amount of from about 58 to about 64 weight percent.

15. The method of claim 12 wherein the 2,3-dichloro-3,3-difluoropropene is present in the amount from about 36 to about 42 weight percent.

16. The method of claim 12 wherein the composition has a boiling point of about 0° C. at a pressure of about 9 psia.

17. The method of claim 12 wherein the composition has a boiling point of from about 25° C. at a pressure of about 23 psia.

18. The method of claim 12 wherein the composition has a boiling point of about 60° C. at a pressure of about 65 psia.

19. The composition of claim 12 having about 61±3 weight percent hydrogen fluoride and about 39±3 weight percent 2,3-dichloro-3,3-difluoropropene at 24° C.

20. A method for removing 2,3-dichloro-3,3-difluoropropene from a mixture containing 2,3-dichloro-3,3-difluoropropene and at least one impurity, which comprises adding hydrogen fluoride to the mixture in an amount sufficient to form an azeotropic or azeotrope-like composition of the 2,3-dichloro-3,3-difluoropropene and the hydrogen fluoride, and thereafter separating the azeotropic composition from the impurity.

21. The method of claim 20 wherein the impurity does not form an azeotropic mixture with 2,3-dichloro-3,3-difluoropropene, hydrogen fluoride or a mixture of 2,3-dichloro-3,3-difluoropropene and hydrogen fluoride.

22. The method of claim 20 wherein the impurity does form an azeotropic mixture with 2,3-dichloro-3,3-difluoropropene, hydrogen fluoride or a mixture of 2,3-dichloro-3,3-difluoropropene and hydrogen fluoride.

23. The process of claim 20 wherein the impurity comprises a halocarbon.

24. The method of claim 20 wherein the impurity is miscible with 2,3-dichloro-3,3-difluoropropene.

25. The method of claim 20 wherein the impurity comprises 1,1,2,3-tetrachloropropene.

26. The method of claim 20 wherein the impurity comprises 2,3,3,3-tetrafluoropropene.

27. The method of claim 20 wherein the impurity comprises 2-chloro-3,3,3-trifluoropropene.

28. The method of claim 20 wherein the impurity comprises 2-chloro-1,1,1,2-tetrafluoropropane.

29. The method of claim 20 wherein the impurity comprises 1,1,1,2,2-pentafluoropropane.

30. The method of claim 20 wherein the impurity comprises 1,2-dichloro-3,3,3-trifluoropropene.

31. The method of claim 20 wherein the impurity comprises 1,1,1,2,3-pentachloropropane.

32. The method of claim 20 wherein the separating is conducted by distillation.

33. The method of claim 20 wherein the azeotropic composition consists essentially of from about 1 to about 80 weight percent hydrogen fluoride and from about 20 to about 99 weight percent 2,3-dichloro-3,3-difluoropropene.

34. The method of claim 20 wherein the azeotropic composition consists essentially of from about 35 to about 70 weight percent hydrogen fluoride and from about 30 to about 65 weight percent 2,3-dichloro-3,3-difluoropropene.

35. The method of claim 20 wherein the azeotropic composition consists essentially of from about 58 to about 64 weight percent hydrogen fluoride and from about 36 to about 42 weight percent 2,3-dichloro-3,3-difluoropropene.

* * * * *